United States Patent [19]

Welter et al.

[11] Patent Number: 5,238,909
[45] Date of Patent: Aug. 24, 1993

[54] 4-SUBSTITUTED ISOXAZOLE HERBICIDES

[75] Inventors: Thomas R. Welter, Webster; John J. Delany, III, Rochester, both of N.Y.

[73] Assignee: Eastman Kodak Company, Rochester, N.Y.

[21] Appl. No.: 583,536

[22] Filed: Sep. 17, 1990

[51] Int. Cl.$^5$ ............................................. A01N 43/80
[52] U.S. Cl. ................................. 504/271; 71/DIG. 1
[58] Field of Search ............... 71/88, 65, 92; 504/271

[56] References Cited

U.S. PATENT DOCUMENTS

| | | | |
|---|---|---|---|
| 2,212,767 | 8/1940 | Blankart | 548/249 |
| 2,556,312 | 6/1951 | Young | 260/333 |
| 3,321,313 | 5/1967 | Burness et al. | 96/111 |
| 4,339,588 | 7/1982 | Kusumi et al. | 548/247 |
| 4,741,763 | 5/1988 | Dürr et al. | 71/92 |
| 4,836,845 | 6/1989 | Schwindeman | 71/92 |
| 4,889,551 | 12/1984 | Oda et al. | 71/88 |

FOREIGN PATENT DOCUMENTS 2-320992 12/1989 Japan .

OTHER PUBLICATIONS

CA 112:193799, Oda et al. (JP 89320992) "Manufacture of isoxazole-4-carboxylic acid . . . etc." 1990.
CA 97:162960t "4 Hydroxy isoxazole . . . etc." *Suntory* JP 8277681, 1975.
"Isolation, Structure and Synthesis of 4-Hydroxyisoxazole (Triumferol), A Seed Germination Inhibitor from an African Plant" by Kusumi et al., Tetrahedron Letters, vol. 22, No. 56, pp. 3451-344 (1981).
Chemical Patents Index, Basic Abstracts Journal, section Ch, week 9007, (Apr. 11, 1990), class C, accession No. 90-047372/07, Derwent Publications Ltd., London, GB; & JP-A-1 320 992 (Human Sci. Shinko Za) Dec. 27, 1989 *Abstract*.
Patent Abstracts of Japan, vol. 13, No. 556 (C-664) [3904], 11th Dec. 1989; & JP-A-1 230 555 (Aguro Kanesho K.K.) Sep. 9, 1989 *Abstract*.
Scientific Reports of Meiji Seika Kaisha, No. 29, 30th Dec. 1990, pp. 26-31, Yokohama, JP; H. Kurihara et al.; "Synthesis of Isoxazole-4-Carboxylic Acid Derivatives and Isoxazole-3, 5-Di-Carboxamides and Their Herbicidal Activities" *Whole Document*.

*Primary Examiner*—Richard L. Raymond
*Assistant Examiner*—B. Bembenick
*Attorney, Agent, or Firm*—Judith A. Roesler

[57] ABSTRACT

A method of controlling plant growth comprising applying to the plants or to a habitat thereof a herbicidally effective amount of a compound having the structure:

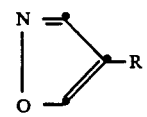

wherein: R is selected from carboxy, carboxylate salt, carboxylate ester, formyl, halomethyl or a substituted methyl group capable of ambient oxidation or hydrolysis to a carboxy group, wherein the substituent on the substituted methyl group consists of an aliphatic group having a heteroatom containing group. The invention is useful in providing an alternative to known herbicidal methods and compositions.

17 Claims, No Drawings

4-SUBSTITUTED ISOXAZOLE HERBICIDES

FIELD OF THE INVENTION

The present invention relates to herbicides.

CROSS-REFERENCE TO RELATED APPLICATIONS

This invention is related to U.S. Ser. No. 07/583,538 entitled "4-Substituted Isoxazoles", filed concurrently herewith, by T. R. Welter and J. J. Delany, III, and commonly owned by and assigned to Eastman Kodak Company, Rochester, N.Y.

BACKGROUND OF THE INVENTION

In the food agricultural industry it is useful to provide the public with a variety of herbicides.

U.S. Pat. No. 4,339,588 dated Jul. 13, 1982 and entitled "Plant Growth Regulators Comprising 4-Hydroxyisoxazole and Related Compounds", assigned to Suntory Limited, Osaka, Japan, discloses that 4-hydroxyisoxazole and its lower alkyl and acyl derivatives having the following structure have herbicidal and plant growth regulating properties:

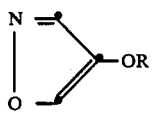

wherein R is hydrogen, lower acyl containing up to 6 carbon atoms, lower alkyl containing up to 6 carbon atoms, substituted and unsubstituted phenyl and benzyl. Although herbicidal properties of 4-hydroxyisoxazole and its lower alkyl and acyl derivatives are disclosed, herbicidal properties of the starting material, 4-isoxazole carboxylic acid, are not disclosed or suggested.

Herbicidally active isoxazolyl imidazoli dinone derivatives are disclosed in U.S. Pat. No. 4, 836,845 entitled "Herbicidally Active Isoxazolyl Imidazolidinone Derivatives" dated Jun. 6, 1989 and assigned to American Cyanamid Company. The American Cyanamid patent does not disclose or suggest that the compounds useful in the methods of this invention have herbicidal properties.

U.S. Pat. No. 3,321,313 entitled "Oxazolium Salts as Hardeners for Gelatin" dated May 23, 1967, assigned to Eastman Kodak Company, Rochester, N.Y. discloses oxazolium salts useful as hardeners for gelatin.

U.S. Pat. No. 4,741,763 entitled "Heterocyclylalkyl Esters Of 2-Imidazolinonenicotinic Acids" dated May 3, 1988 assigned to CIBA Geigy discloses compounds of the structure:

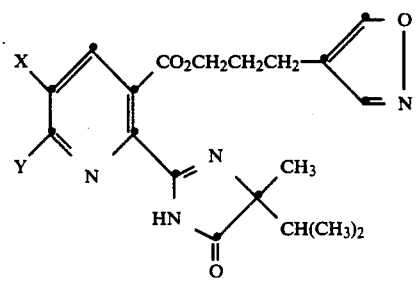

which are used as herbicides.

SUMMARY OF THE INVENTION

We have developed a method of controlling plant growth which provides an alternative to existing methods.

More specifically, in accordance with the present invention, there is provided a method of controlling plant growth comprising: applying to the plants or to a habitat thereof a herbicidally effective amount of a compound having the structure:

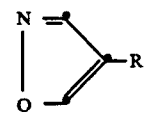

wherein

R is selected from carboxy, carboxylate salt, carboxylate ester, formyl, halomethyl or a substituted methyl group capable of ambient oxidation or hydrolysis to a carboxy group, wherein the substituent on the substituted methyl group consists of an aliphatic group having a heteroatom containing group.

In accordance with another aspect of the invention, there is provided a method of controlling plant growth comprising applying to the plants or to a habitat thereof a herbicidally effective amount of a compound having the structure:

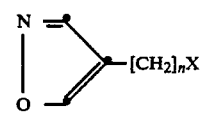

wherein n is 2 or 3 and X is acetcxy, phenoxycarbonyl benzyloxycarbonyl, pentoxycarbonyl, t-butoxycarbonyl, pentadecyloxycarbonyl, carboxypheroxycarbonyl, oxy-2-tetrahydropyranyl, butoxycarbonyloxy, N-methylcarbamoyloxy, N-methyl N-phenylcarbamoyloxy, N-(3-chlorophenyl)carbamoyloxy, methylsulfonyloxy, tosyloxy, phenoxy, carboxy, carbamoyl, anilinocarbonyl, 4-methoxyanilinocarbonyl, 4-chloroanilinocarbonyl, dichloroanilinocarbonyl, 4-(carboxyethyl)anilinocarbonyl, 3-trifluoromethylanilinocarbonyl 4-propylanilinocarbonyl, 4-cyanoanilinocarbonyl, 4-methanamidoanilinocarbonyl, 4-nitroanilinocarbonyl, 4-phenylsulfonylanilinocarbonyl, 4-benzenesulfonamidoanilinocarbonyl.

In accordance with still another aspect of the invention, there is provided a method of controlling plant growth comprising applying to the plants or to a habitat thereof a herbicidally effective amount of a compound having the structure:

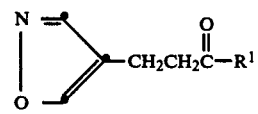

wherein $R^1$ is selected from hydroxy, alkoxy wherein the alkyl portion has 1 to 10 carbon atoms and consists of an aliphatic group, meta or para substituted phenoxy, amino, unsubstituted anilino, meta substituted anilino, para substituted anilino, and alkylamino wherein the alkyl portion has 1 to 10 carbon atoms and consists of a straight-chain aliphatic group having a hetero atom containing group.

In accordance with a further aspect of the invention, there is provided a herbicidal composition containing an inert carrier, and, as an active ingredient, an effective amount of a compound according to the formulas as described above.

In accordance with a still further aspect of the invention, there is provided a solid herbicidal composition comprising a surfactant in an amount effective to prevent crystallization of the herbicide and a herbicidal composition according to the formulas as described above.

In accordance with another aspect of the invention, there is provided a wettable powder herbicidal composition comprising from about 25% to about 75% of a solid solution of a surfactant in an amount effective to prevent crystallization of the herbicide and a herbicidal composition according to the formulas as described above, and from about 75% to about 25% of a solid carrier.

It is an advantageous feature of this invention that it provides an alternative to existing herbicidal methods.

It is also an advantageous feature of this invention that it provides a herbicidal method using a class of herbicides which combine the features of effectiveness and stability over a long period of time.

DESCRIPTION OF THE PREFERRED EMBODIMENTS

The invention provides a method of controlling plant growth comprising applying to the plants or to a habitat thereof a herbicidally effective amount of a compound having the structure

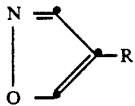

wherein

R is selected from carboxy, carboxylate salt, carboxylate ester, formyl, halomethyl including dihalomethyl and trihalomethyl wherein the halogen atom is chloro, bromo, iodo, or fluoro, or a substituted methyl group capable of ambient oxidation or hydrolysis to a carboxy group wherein the substituent on the substituted methyl group consists of an aliphatic group having a heteroatom-containing group. Substituted methyl groups capable of ambient oxidation to a carboxy group are well known in the art, such as 3-acetoxypropyl. Preferred substituted methyl groups are carboxyalkenyl or esters thereof or haloalkenyl groups wherein the carboxy group (carboxylate ester) or the halo atom is appended to an unsaturated carbon of the alkenyl group. Examples of such carboxyalkenyls or haloalkenyls are 2-carboxyvinyl, 2-ethoxycarbonylvinyl, 1-bromo-1-propenyl and 1-bromo-1-octenyl.

Ambient oxidation is defined for the purposes of this invention as oxidation by natural surroundings as opposed to oxidation using chemicals or temperature variations.

The oxidation mechanisms which the substituted methyl groups undergo include Δ-oxidation mechanisms, β-oxidation mechanisms, and other oxidation mechanisms which are well known in the art. Examples of substituted methyl groups not capable of beta oxidative activation include hydroxyethyl and 2-methyl 3-hydroxypropyl.

Preferred substituted methyl groups include ones that are capable of direct oxidation, such as hydroxymethyl or formyl, and ones that are capable of β-oxidation, such as hydroxypropyl.

Examples of straight chain aliphatic groups having a hetero atom containing group including nitrogen, oxygen and sulfur, which are in, or directly appended via the hetero atom to, the aliphatic chain which are useful within the scope of this invention include carboxyethyl, acetoxypropyl, benzyloxycarbonylethyl, pentoxycarbonylpropyl, t-butoxycarbonylbutyl, phenoxycarbonylpropyl, benzyloxycarboxylpropyl, N-methylcarbamoyloxypropyl, methylsulfonyloxypropyl, tosyloxypropyl, carbamoylethyl, N,N-h(2-hydroxyethyl) carbamoylethyl, N-phenylcarbamoylethyl, N-(4-chlorophenyl)carbamoylethyl, N-(3,4-dichlorophenyl)carbamoylethyl, and 2-[3-(4-isoxazolyl)propoxycarbonyl]ethyl.

The invention also provides a method of controlling plant growth comprising applying to the plants or to a habitat thereof a herbicidally effective amount of a compound having the structure:

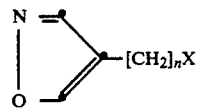

wherein n is 2 or 3 and X is acyloxy, such as acetoxy, aryloxycarbonyl, such as phenoxycarbonyl, carboxyphenoxycarbonyl, alkoxycarhonyl such as benzyloxycarbonyl, methoxycarbonyl, pentoxycarbonyl, t-butoxycarbonyl, pentadecyloxycarbonyl, heterocyclyloxy, such as 2-tetrahydropyranyloxy, alkoxycarbonyloxy such as butoxycarbonyloxy, carbamoyloxy such as N-methylcarbamoyloxy, N-methyl-N-phenylcarbamoyloxy, N-(3-chlorophenyl)carbamoyloxy, alkylsulfonyloxy, such as methylsulfonyloxy and arylsulfonyloxy, such as tosyloxy, carboxy, carbamoyl, such as N-phenylcarbamoyl, N-(4-methoxyphenyl)carbamoyl, N-(4-chlorophenyl)carbamoyl, N-(dichlorophenyl)carbamoyl, N-(4-carboxyphenyl)carbamoyl, N-(3-trifluoromethylphenyl)carbamoyl, N-(4-propylphenyl)carbamoyl, N-(4-cyanophenyl)carbamoyl, N-(4-methanamidophenyl)carbamoyl, N-(4-nitrophenyl)carbamoyl, N-(4-phenylsulfonylphenyl)carbamoyl, N-(4-benzenesulfonamidophenyl)carbamoyl.

Examples of X for the method described above wherein n is 3 are acetoxy, phenoxycarbonyl, benzyloxycarbonyl, pentoxycarbonyl, t-butoxycarbonyl, pentadecyloxycarbonyl, carboxyphenoxycarbonyl, oxy-2-tetrahydropyranyl, butoxycarbonyloxy, N-methylcarbamoyloxy, N-methyl N-phenylcarbamoyloxy, N-(3-chlorophenyl)carbamoyloxy, methylsulfonyloxy, tosyloxy. Preferred compounds for the method described above include compounds wherein n is 3 and X is acetoxy, phenoxycarbonyl, butoxycarbonyloxy, methylsulfonyloxy and tosyloxy.

Examples of X for the method described above wherein n is 2 are carboxy, methoxycarbonyl, ethoxycarbonyl, carbamoyl, N-(pheryl)carbamoyl, N-(4-methoxyphenyl)carbamoyl, N-(4-chlorophenyl)carbamoyl, N-(dichlorophenyl)carbamoyl, N-(4-carboxyphenyl)carbamoyl, N-(3 trifluoromethylphenyl)carbamoyl, N-(4-propylphenylcarbamoyl, N-(4-cyanophenyl)carbamoyl, N-(4-methanamidophenyl)carbamoyl, N-(4-nitrophenyl)carbamoyl, N-(phenylsulfonylphenyl)carbamoyl, N-(4-benzenesulfonamidophenyl)carbamoyl.

The invention further provides a method of controlling plant growth comprising applying to the plants or to a habitat thereof a herbicidally effective amount of a compound having the structure:

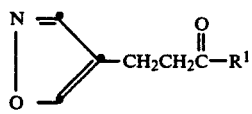

wherein R$^1$ is selected from
(1) hydroxy;

(2) alkoxy wherein the alkyl portion has 1 to 10 carbon atoms and such as methoxy, ethoxy, propoxy, butoxy, and pentoxy;
(3) meta substituted phenoxy, para substituted phenoxy, and meta, para substituted phenoxy and tri-substituted phenoxy, wherein the substituents comprise substituted or unsubstituted alkyl of 1 to 4-carbon atoms such as methyl, ethyl, propyl, butyl, carboxyethyl, alkoxy of 1 to 4-carbon atoms such as methoxy, ethoxy, propoxy, butoxy, halo such as chloro, iodo, fluoro, bromo, including dihalo and trihalo such as 3,4-dichloro and trifluoro, cyano, nitro, phenylsulfonyl, benzamido, alkylformamido of 1 to 5 carbon atoms and benzenesulfonamido;
(4) amino and alkylamino including dialkylamino wherein the alkyl portion is substituted or unsubstituted and has 1 to 10 carbon atoms, such as methyl, ethyl, carboxyethyl, and so on; and
(5) anilino, meta substituted anilino and para substituted anilino wherein the substituents comprise substituted or unsubstituted alkyl of 1 to 4 carbon atoms, alkoxy of 1 to 4 carbon atoms, halo, cyano, nitro, phenylsulfonyl, benzamido, alkylformamido of 1 to 5 carbon atoms and benzenesulfonamido.

Compounds of this class are particularly stable while having good herbicidal activity and are therefore, preferred.

The preparation of 4-substituted isoxazoles is disclosed in U.S. Pat. No. 3,321,313 discussed above wherein the preparation of 4-(3-hydroxypropyl)-isoxazole is disclosed. In general, 4-substituted isoxazoles are prepared according to the following reaction schemes.

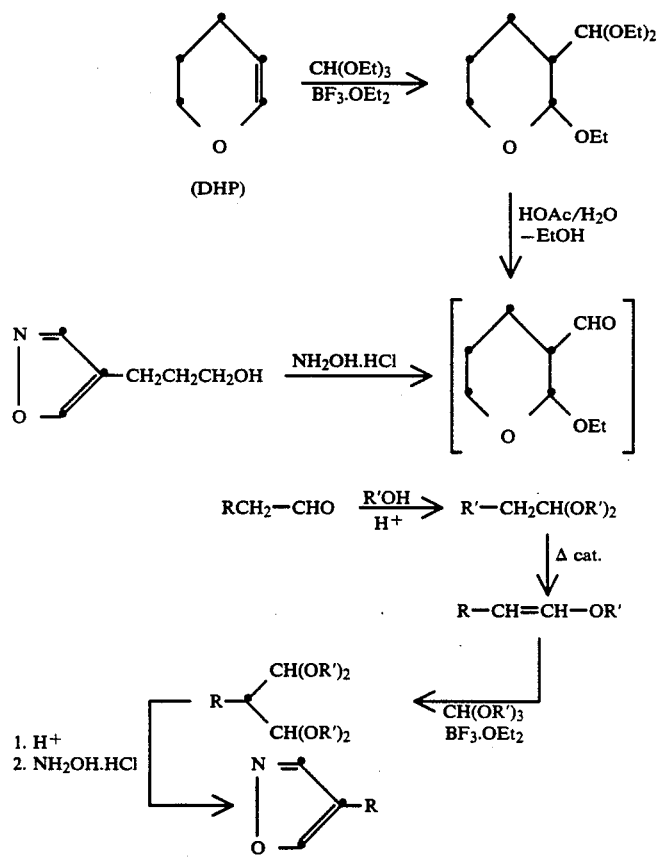

In general, aldehydes adjacent methylene groups may be converted to their corresponding enol ethers via acetal formation following by pyrolysis. These ethers give rise to malonaldehyde bis-acetals upon treatment with orthoformate esters in the presence of Lewis acid catalysis (e.g. borontrifluoride etherate). These acetals, either treated with aqueous acid followed by hydroxylamine hydrochloride or treated directly with aqueous hydroxylamine hydrochloride, yielded the corresponding isoxazoles. Alternative methods for the preparation of enol ethers include Wittig reaction of aldehydes with ylides derived from methoxyphosphonium salts) as disclosed by G. Wittig and M. Schlosser in Chem. Ber., 94:1373 (1961) or malonaldehyde derivatives through Vilsmeier reaction of various substrates to yield enamines of malonaldehyde as disclosed by Z. Arnold and M. Budesinsky in the Journal of Organic Chemistry, 53:5352 (1988)). The synthesis and properties of isoxazoles are further disclosed in "The Chemistry of Heterocyclic Compounds", Vol. 17, R. Wiley, Ed., Interscience Publishers, New York, (1962), "Heterocyclic Compounds, R. Elderfield, Ed., John Wiley and Sons, Inc., N.Y. (1957) and "Comprehensive Heterocyclic Chemistry" by A. Katritzky and C. Rees, Eds., Pergamon Press, N.Y. (1985). Isoxazoles unsubstituted upon carbon 3 are base unstable. They decompose to form alpha cyano carbonyl derivatives. Base sensitivity is increased with electron withdrawing substitution. Under reducing conditions, the isoxazole nitrogen to oxygen bond may be cleaved. Isoxazoles are generally very stable to strong acids, including concentrated sulfuric acid.

Application of the compounds which are usaful in the process of the invention for Purposes of herbicidal control can be accomplished employing both conventional type formulation and equipment. The compounds may, for instance, be formulated as wettable powders, dusts, dust concentrates, emulsifiable concentrates and the like which are amenable to application with conventional spraying or dusting apparatus.

For use in agriculture, the herbicides as useful in this invention may be advantageously formulated as a wettable powder. Wettable powders are usually prepared by grinding and milling the ingredient with a solid carrier, such as kaolin, diatomaceous earth, synthetic calcium silicate, fullers earth (calcium montmorillonite), talc, pumice, and the like. Usually, about 25% to 75% by weight of solid carrier, is used. In addition, there is generally added about 1% to 5% by weight of a dispersing agent, such as alkali metal salts of naphthalene sulfonic acid and anionic nonionic blends, and from about 1% to 5% by weight of a surfactant, such as polyoxyethylene alcohols, acids, adducts, sorbitan fatty acide esters. sorbital esters, and the like. The amount of solid carrier is then reduced accordingly to compensate for the amount of dispersing agent(s) and surfactant(s) incorporated into the formulation.

Wettable powders are prepared in the same manner as the dust concentrates excepting that about 1% to 5% by weight of a dispersing agent such as the calcium salt of a polymerized alkyl aryl sulfonic acid, sodium lignosulfate, or sodium salt of condensed naphthalene sulfonic acid is blended with the mixture and about 1% to 5% of a surfactant, such as polyoxyethylated vegetable oil, alkyl phenoxy polyoxyethylene ethanol, sodium alkyl naphthalene sulfonate is also blended with the formulation.

Wettable powder formulations are generally prepared by admixing from about 25 percent to about 95 percent, by weight, of active ingredient with finely ground clay, such as kaolin or attapulgite, either with or without a surface active agent. emulsifier or spreader sticker. The latter is then dispersed in water for spray application.

Wettable powders are usually dispersed in water and applied as dilute aqueous sprays at a rate of 0.28 kg to 22.4 kg/hectare of active ingredient to the area where control of undesirable plant species is desired.

In practice, the wettable powder is dispersed in water and applied as a liquid spray to the foliage of undesirable plants. Application rates should be sufficient to provide about 0.25 to 10 pounds per acre of the pyrazolium salt and, although 0.5 to 5.0 pounds per acre of said salt is generally satisfactory to control undesirable broadleaf weeds and undesirable grass plants, it should be recognized that rates exceeding 10 and as high as 20 pounds per acre can be used. These higher rates would, of course, be used in areas such as railroad sidings, beneath power lines and along hedge rows bordering property l:nes and fields.

Advantageously, many of the compounds useful in the process of this invention demonstrate a high degree of water solubility and lend themselves to the preparation of aqueous concentrates. Among the preferred salts are the alkali metal salts, ammonium salts or alkylammonium salts. In practice, the aqueous concentrates may be applied directly as a liquid spray to the foliage of undesirable broadleaf weeds and grassy plants. Alternatively, they may be further diluted with water and applied as dilute aqueous sprays to these undesirable plants.

The water miscible concentrates are prepared by dissolving a wide range of percentages of one or more compounds of the invention in a water miscible solvent, such as water itself or another polar water miscible solvent, such as 2-methoxyethanol, methanol, propylene glycol, diethylene glycol, diethylene glycol monoethyl ether, formamide, and dimethylformamide. Application of the material is made by adding a predetermined quantity of the water miscible concentrate to a spray tank and applying the mixture as such or in combination with a suitable diluent, such as a further quantity of water or one of the above polar solvents.

The performance of the product in all of the above formulations, which are applied as liquid sprays, is expected to improve by the addition of a surfactant or blend of surfactants. Conventional anionic, cationic and nonionic surfactants may be employed.

Illustrative nonionic surfactants are: alkyl polyoxyethylene ethers, polyoxethylene (20) sorbitan monolaurate, polyoxyethylene (20) sorbitan monoleate, alkylarylpolyglycol ethers, alkyl phenol ethoxylates, trimethyl nonyl polyethylene glycol ethers alkyl phenol ethylene oxide condensates, octyl phenoxy polyethoxy ethanols, nonylphenyl polyethylene glycol ethers, condensates of polyoxy ethylenes, polyoxypropylenes, aliphatic polyethers, aliphatic polyesters, alkylaryl polyoxyethylene glycols, and the like.

Exemplary anionic surfactants include sodium dodecylbenzene sulfonate and the dioctyl ester of sodium sulfosuccinic acid.

Suitable cationic surfactants include dicoco dimethylammonium chloride, steararmidopropyl dimethyl betahydroxyethylammonium nitrate and the like.

These surfactants are preferably added to the spray tank at the rate of 0.1% to 5% by volume to provide good wetting of the spray solution on plant foliage.

Herbicidal concentrates containing surfactants are preferably formulated as aqueous sprays containing approximately 30% by weight of the appropriate salt, from about 25% to 50% by weight of water and the remainder of said formulation (25% 45% weight) of a selected surfactant. Surfactants which are especially useful in preparing suitable surfactant containing concentrates include an octylphenol ethylene oxide condensate, an ethanolic solution of an alkylphenol ethoxylate, a polyglycolic ether condensate produced from ethylene oxide and an alkyl phenol, and an alkyl aryl polyglycolic ether.

Dusts are generally prepared by grinding together about 1% to 25% by weight of the active agent with from about 99% to 75% by weight of a solid diluent such as kaolin, attapulgite, talc, pumice, diatomaceous earth, fullers earth (calcium montmorillonite), wood flour, or the like.

Dust concentrates are prepared in similar fashion excepting that about 25% to 95% by weight of the active agent is ground with about 75% to 5% by weight of the diluent.

Dusts and dust concentrates are similarly prepared using from about 5 percent to about 95 percent of active ingredient and from about 95 to about 5 percent of finely divided inert ingredients. These dusts are generally applied as such, or they may be further diluted with finely ground inert solids and then applied with conventional dusting apparatus.

Emulsifiable concentrates may be prepared by dissolving or dispersing the active ingredient and organic solvent, with or without emulsifying agents, surfactants or the like. Such formulations are then diluted with either water or an appropriate organic diluent prior to application.

For application of the compounds useful in the process of this invention to the foliage of the undesirable plant species, the compounds are generally formulated as postemergence herbicidal compositions by admixing a herbicidal adjuvant with a herbicidally effective amount of the compound. Suitable adjuvants include one or more conventionally solid or liquid carriers, diluents and formulation aids, particularly surfactants.

EXAMPLE I

Bioassay of Potential Herbicides—Primary Screen 7.5×7.6×6 cm units are filled with steam sterilized soil and held in greenhouse flats (43 ×43×5 cm). The depth of planting and number of seeds per unit varies with each species.

Weeds tested include:

| | Abbreviation |
|---|---|
| a. Barnyard grass (*Echinochloa crusgalli*) | BYGRASS |
| b. Green foxtail (*Setaria viridis*) | FOXTAIL |
| c. Wild oats (*Avena fatua*) | WILDOAT |
| d. Nightshade (Solanum sp.) | NSHADE |
| e. Velvetleaf (*Abutilon theophrasti*) | VLEAF |
| f. Annual morningglory (*Ipomoea purpurea*) | MGLORY |
| h. Yellow nutsedge (*Cyperus esculentus*) | YNUTSED |
| i. Pigweed (*Amaranthus retroflexus*) | PWEED |
| j. Downy brome (*Bromus teotorum*) | DBROME |

Rationale for selection of these species include:
a. Affected plants are indicators of symptomology of herbicides.
b. One or more species is sensitive to all United States commercial herbicides at the 4 pounds per acre rate.
c. Each species represents a different genus.
d. Economic importance.
e. Will germinate within 7 days and grow very well every month of the year.
f. Available source of viable seeds.

Germination tests are routinely conducted on new shipments of weeds to establish a baseline viability.

Preemergence test: Seeds are planted in a sandyloam soil mixture (3 parts sandy loam soil to 1 part perlite). Weed seeds are planted at the following densities using a volumetric measurement.

| Weed Species | No. Seeds/Pot |
|---|---|
| Barnyardgrass | 50 |
| Green foxtail | 45 |
| Wild oats | 55 |
| Nightshade | 35 |
| Velvet leaf | 20 |
| Annual Morningglory | 10 |
| Yellow nutsedge | 10 |
| Pigweed | 35 |
| Downy brome | 50 |

Postemergence test: Seeds are planted as described above except supersoil .fir bark, redwood, Canadian peat, and sand) is used. Plants are fertilized weekly with a 10:10:10 fertilizer mix.

Seedlings are thinned to the following densities:

| Weed Species | No. Seeds/Pot |
|---|---|
| Barnyardgrass | 40 |
| Green foxtail | 40 |
| Wild oats | 40 |
| Nightshade | 20 |
| Velvet leaf | 20 |
| Annual Morningglory | 5 |
| Yellow nutsedge | 5 |
| Pigweed | 10 |
| Downy brome | 4 |

The preemergence test consists of spraying the soil surface with the test corpound at 4 pounds active ingredient (ai) per acre using a belt sprayer equipped with an overhead nozzle. A mixture of an octylphenoxy polyethoxy ethanol surface active agent, a polyoxyethylene sorbitan monolaurate surface active agent, and a sorbitan monolaurate surface active agent is added at 1000 ppm to increase spreadability of the compound. The compound is applied at 100 gallons per acre and 21.9 grams per square inch, and the belt speed is 0.5 miles per hour. Spraying is done within 6 hrs. after planting. The soil is watered shortly after treatment and receives daily watering of a fine mist. Little or no drainage of water out of the cup bottoms occur.

Postemergence tests involve spraying of established seedlings using the same equipment and formulation as noted above. Weeds used in postemergence studies are held in moist soil without additional watering for 48 hrs. and then receive daily watering of a fine mist spray.

A test consists of
a. Control—seed only
b. Test—seed plus compound
c. Standard

One replicate of each test is conducted. The level of control is periodically evaluated with a written evaluation at one and two weeks posttreatment.

The percentage preemergence weed control is assessed using a ranking of 0 to 4,

| Ranking | |
|---|---|
| 0 | Near 100% germination, no phytotoxicity observed. |
| 1 | Near 75% seed germination, no phytotoxicity to seedlings. |
| 2 | Seed germination delayed, over 50% seed germination, and/or some phytotoxicity. |
| 3 | Less than 50% seed germination and/or extensive phytotoxicity to established plants. |
| 4 | No observed germination and/or establishment. |

-continued

| Ranking | |
|---|---|
| | Postemergence evaluation: |
| 0 | No chlorosis, suppression or inhibition of plant growth, etc. observed. |
| 1 | Minimal phytotoxicity, plants generally healthy. |
| 2 | Less than 50% plant injury, recovery evident. |
| 3 | Over 50% plant injury, some plant death. |
| 4 | All plants dead with no recovery. |

The test results are reported in Tables I, II and III.

TABLE I

Derivatives of 3-(4-Isoxazolyl)propan-1-ol

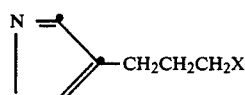

| Compound | X | PRE | POH |
|---|---|---|---|
| 1 | OAc | 1.6 | 2.6 |
| 2 | OCOPh | 1.8 | 1.3 |
| 3 | OCOCH$_2$Ph | 1.3 | 1.2 |
| 4 | OCO-n-C$_5$H$_{11}$ | 1.4 | 1.3 |
| 5 | OCO-t-Bu | 1.1 | 1.9 |
| 6 | OCO-n-C$_{15}$H$_{31}$ | 1.3 | 1.1 |
| 7 | OCO-2-(CO$_2$H)Ph | 1.4 | 1.9 |
| 8 | 2-Tetrahydropyranyloxy | 1.3 | 0.9 |
| 9 | OCO$_2$-n-Bu | 1.6 | 1.2 |
| 10 | OCONMePh | 1.3 | 1.6 |
| 11 | OCONH-3-ClPh | 0.8 | 1.4 |
| 12 | OMs | 1.7 | 0.9 |
| 13 | OTs | 1.7 | 1.1 |
| 14 | OH | 1.8 | 2.15 |

TABLE II 3-(4-Isoxazolyl)propanoic Acid and Derivatives

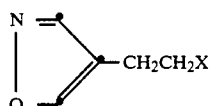

| Compound | X | PRE | POH |
|---|---|---|---|
| 15 | CO$_2$H | 1.8 | 2.6 |
| 16 | CO$_2$Me | 2.1 | 2.2 |
| 17 | CONH$_2$ | 2.4 | 2.4 |
| 18 | CON(CH$_2$CH$_2$OH)$_2$ | 0.8 | 1.4 |
| 19 | CONHPh | 1.9 | 2.2 |
| 20 | CONH-4-ClPh | 2.1 | 2.7 |
| 21 | CONH-3,4-Cl$_2$Ph | 1.9 | 2.4 |
| 22 | CO$_2$(CH$_2$)$_3$-4-isoxazolyl | 1.1 | 2.1 |

TABLE III

Further Oxidized Isoxazoles Tested

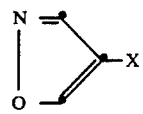

| Compound | X | PRE | POH |
|---|---|---|---|
| 23 | CH$_2$CO$_2$H | 1.3 | 1.9 |
| 24 | CO$_2$H | 2.3 | 2.4 |
| 25 | CO$_2$Et | 1.6 | 2.6 |
| 26 | CO$_2$-n-C$_5$H$_{11}$ | 1.4 | 1.9 |
| 27 | CO$_2$CH$_2$CH$_2$OMe | 1.4 | 2.1 |
| 28 | CO$_2$-i-Pr | 1.2 | 1.3 |
| 29 | CO$_2$CH$_2$Ph | 1.3 | 2.1 |

TABLE III-continued

Further Oxidized Isoxazoles Tested

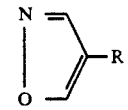

| Compound | X | PRE | POH |
|---|---|---|---|
| 30 | CO$_2$-4-ClPh | 1.6 | 2.1 |
| 31 | CO$_2$(pyridinium)+ | 2.6 | 2.6 |
| 32 | CH$_2$OH | 1.9 | 2.0 |
| 33 | CHO | 1.2 | 1.9 |
| 34 | CH=NOH | 1.9 | 2.1 |
| 35 | CH=N—NHPh | 1.6 | 1.8 |
| 36 | CH$_2$OAc | 2.8 | 1.9 |
| 37 | CH$_2$OCOPh | 0.9 | 2.0 |
| 38 | CH$_2$OCONHPh | 1.2 | 0.9 |
| 39 | CH$_2$Br | 1.6 | 1.6 |
| 40 | CHBr$_2$ | 1.6 | 1.9 |
| 41 | CBr$_3$ | 1.1 | 1.7 |
| 42 | CH$_2$O(CH$_2$)$_4$OCOCF$_3$ | 1.3 | 1.8 |
| 43 | CH=CHCOOEt | 1.0 | 1.4 |
| 44 | C(Br)=CHCH$_3$ | 0.0 | 0.7 |
| 45 | CH=CHCOOH | 1.6 | 1.6 |
| 46 | C(Br)=CH-n-C$_6$H$_{13}$ | 0.8 | 0.8 |

The invention has been described in detail with particular reference to certain preferred embodiments thereof, but it will be understood that variations and modifications can be effected within the spirit and scope of the invention.

What is claimed is:

1. A method of controlling plant growth comprising applying to the plants or to a habitat thereof a herbicically effective amount for growth regulation of a compound having the structure:

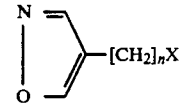

wherein R is selected from carboxy, carboxylate salt, carboxylate ester, formyl, halomethyl or a substituted methyl group capable of ambient oxidation to a carobxy group wherein the substituent on the substituted methyl group consists of a straight chain aliphatic group having a heteroatom-containing group in or directly appended via the hetero atom to the aliphatic chain, wherein the hetero atom is selected from nitrogen, oxygen or sulfur.

2. A method according to claim 1 wherein halomethyl includes dihalomethyl and trihalmethyl.

3. A method of controlling plant growth comprising applying of the plants or to a habitat thereof a herbicidally effective amount for growth regulation of a compound having the structure:

wherein n is 2 or 3 and X is acetoxy, phenoxycarbonyl, benzyloxycarbonyl, pentoxycarbonyl, t-butoxycarbonyl, pentadecyloxycarbonyl, carboxyphenoxycarbonyl, 2-tetrahydropyranyloxy, butoxycarbonyloxy, N-methylcarbamoyloxy, N-methyl-N-phenylcarbamoyloxy, N-tolylcarbamoyloxy, N-(3-chlorophenyl)- carbamoyloxy, methylsulfonyloxy, tosyloxy, phenoxy, carboxy, carbamoyl, anilinocarbonyl, 4-methoxyanilinocarbonyl, 4-chloroanilinocarbonyl, dichloroanilinocarbonyl, 4-carboxyethylanilinocarbonyl, 3-trifluoromethylanilinocarbonyl, 4-propylanilinocarbonyl, 4-cyanoanilinocarbonyl, 4-methanamidoanilinocarbonyl, 4-nitroanilinocarbonyl, 4-phenylsulfonylanilinocarbonyl or 4-benzenesulfonamidoanilinocarbonyl.

4. A method according to claim 3 wherein n is 3 and X is acetoxy, phenoxycarbonyl, benzyloxycarbonyl, pentoxycarbonyl, t-butoxycarbonyl, pentadecyloxycarbonyl, carboxyphenoxycarbonyl, 2-tetrahydropyranyloxy, butoxycarbonyloxy, N-methylcarbamoyloxy, N-methyl-N-phenylcarbamoyloxy, N-tolylcarbamoyloxy, N-(3-chlorophenyl)carbamoyloxy, methylsulfonyloxy, tosyloxy.

5. A method according to claim 4 wherein X is acetoxy, phenoxycarbonyl, butoxycarbonyloxy, methylsulfonyloxy and tosyloxy.

6. A method according to claim 3, wherein n is 2 and X is carboxy, methoxycarbonyl, ethoxycarbonyl, carbamoyl, anilinocarbonyl, 4-methoxyanilinocarbonyl, 4-chloroanilinocarbonyl, dichloroanilinocarbonyl, 4-carboxyanilinocarbonyl, 3-trifluoromethylanilinocarbonyl, 4-propylanilinocarbonyl, 4-cyanoanilinocarbonyl, 4-proprionamidoanilinocarbonyl, 4-nitroanilinocarbonyl, 4-phenylsulfonylanilinocarbonyl, 4-benzenesulfonamidoanilinocarbonyl.

7. A method of controlling plant growth comprising applying to the plants or to a habitat thereof a herbicidally effective amount for growth regulation of a compound having the structure:

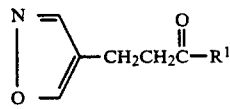

wherein $R^1$ is selected from;
(1) hydroxy;
(2) an alkoxy having from 1 to 10 carbon atoms;
(3) meta substituted phenoxy, para substituted phenoxy, meta, para substituted phenoxy, or tri-substituted phenoxy, wherein said substituents on the phenoxy are selected from the group consisting of alkyl of 1 to 4 carbon atoms, carboxyethyl, alkoxy of 1 to 4 carbon atoms, halo, dihalo, and trihalo, cyano, nitro, phenylsulfonyl, benzamido, alkylformamido of 1 to 5 carbon atoms, and benzenesulfonamido;
(4) and alkylamino wherein the alkyl portion has from 1 to 10 carbon atoms;
(5) unsubstituted anilino, metal substituted anilino, and para substituted anilino, are selected from alkyl of 1 to 4 carbon atoms, alkoxy of 1 to 4 carbon atoms, cyano, nitro, phenylsulfonyl, benzamido, alkylformamido of 1 to 5 carbon atoms or benzenesulfonamido.

8. A method according to claim 7, wherein said compound is selected from said metal or para substituted anilino.

9. A method according to claim 7, wherein said compound is selected from said meta substituted phenoxy, said para substituted phenoxy, or said metal, para phenoxy.

10. A method according to claim 7 wherein $R^1$ is selected from the group consisting of hydroxy, methoxy, amino, annilino, 4-methoxyanilino, 4-chloroanilino, 3,4-dichloroanilino, 3-carboxyethylanilino, 4-carboxyethylanilino, 3-trifluoromethylanilino, 4-propylanilino, 4-cyanoanilino, propionamidoacetamido, 4-nitroanilino, 4-phenylsulfonylanilino, or 4-benzenesulfonaminoanilino.

11. A herbicidal dust which contains from about 5 percent to about 95 percent by weight of inert ingredients comprising an inert carrier, and, as an active ingredient, from about 5 percent to about 95 percent by weight of a 4-substituted isoxazole according to claim 1.

12. A herbicidal dust which contains from about 5 percent to about 95 percent of inert ingredients comprising an inert carrier, and, as an active ingredient, from about 5 percent to about 95 percent by weight of a 4-substituted isoxazole according to claim 7.

13. A wettable powder herbicial composition comprising a surfactant, a dispersing agent, a solid carrier and, as an active ingredient, the 4-substituted isoxazole according to claim 1.

14. A solid herbicidal composition comprising a surfactant in an amount effective to prevent crystallization of the herbicide and a herbicidal composition of the formula according to claim 8.

15. A wettable powder herbicidal composition comprising a surfactant, a solid carrier and, as an active ingredient, the 4-substituted isoxazole according to claim 7.

16. A method of controlling plant growth comprising applying to the plants or to a habitat thereof a herbicially effective amount for growth regulation of a compound having the structure:

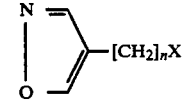

wherein n is 3 and x is acetoxy, phenoxycarbonyl, benzyloxycarbonyl, pentoxycarbonyl, t-butoxycarbonyl, pentadecycloxycarbonyl, carboxyphenoxycarbonyl, 2-tetrahydropyranyloxy, butoxycarbonyloxy, N-methylcarbamoyloxy, N-methyl-N-phenylcarbamoyloxy, N-tolylcarbamoyloxy, N-(3-chlorophenyl)-carbamoyloxy, methylsulfonyloxy, or tosyloxy.

17. A method according to claim 13 wherein x is acetoxy, phenoxycarbonyl, butoxycarbonyl, methylsulfonyl or tosyloxy.

* * * * *